United States Patent
Gast

(10) Patent No.: US 8,758,775 B2
(45) Date of Patent: Jun. 24, 2014

(54) PHARMACEUTICAL COMPOSITION INCLUDING CLINOPTILOLITE

(76) Inventor: Kevin Gast, Pretoria (ZA)

( * ) Notice: Subject to any disclaimer, the term of this patent is extended or adjusted under 35 U.S.C. 154(b) by 1171 days.

(21) Appl. No.: 12/066,338

(22) PCT Filed: Sep. 8, 2006

(86) PCT No.: PCT/IB2006/053178
§ 371 (c)(1),
(2), (4) Date: May 16, 2008

(87) PCT Pub. No.: WO2007/029208
PCT Pub. Date: Mar. 15, 2007

(65) Prior Publication Data
US 2008/0226683 A1 Sep. 18, 2008

(30) Foreign Application Priority Data
Sep. 10, 2005 (ZA) ...................................... 05/4769

(51) Int. Cl.
*A61K 33/06* (2006.01)
*A61P 1/00* (2006.01)
*C01B 39/26* (2006.01)

(52) U.S. Cl.
CPC ................. *A61K 33/06* (2013.01); *C01B 39/26* (2013.01)
USPC .......................... 424/278.1; 424/684; 423/700

(58) Field of Classification Search
USPC .............................................. 424/278.1, 684
See application file for complete search history.

(56) References Cited

U.S. PATENT DOCUMENTS

| | | | | |
|---|---|---|---|---|
| 5,116,793 A * | 5/1992 | Chao et al. | ....................... | 502/68 |
| 2005/0031708 A1* | 2/2005 | Portney | .......................... | 424/684 |
| 2005/0106267 A1* | 5/2005 | Frykman et al. | .............. | 424/684 |

FOREIGN PATENT DOCUMENTS

WO 02100420 12/2002

OTHER PUBLICATIONS

Athanasiadis et al, Influence of chemical conditioning on the ion exchange capacity and on kinetic of zinc uptake by clinoptilolite, Water Research 39 (2005) 1527-1532.*
Sprynskyy et al. Journal of Colloid and Interfacial Science. pp. 408-415, Available on line Dec. 23, 2004.*
Mineral Supplies International (MSI-Zeoclere—Jan. 30, 2013) (http://www.pool-chem.co.uk/prodpdf/Zeoclere%2030%20Specification.pdf).*
International Aquatics (pp. 1-28, Jul./Aug. 2001)( http://www.alisonosinski.com/wp-content/pdf/chloramines.pdf).*
Aqua Leisure (2006) (http://www.freewebs.com/arcticspas-southampton/filtermediareplacement.htm).*
Athanasiadis, et al., "Influence of chemical conditioning on the ion exchange capacity and on kinetic of zinc uptake by clinoptilolite," Water Research, Elsevier, Amstersam, NL, vol. 39, No. 8, Apr. 2005, pp. 1527-1532.
Rivera et al., "Preliminary characterization of drug support systems based on natural clinoptilolite," Microporous and Mesoporous Materials, Elsevier Science Publishing, New York, US, vol. 61, No. 1-3, Jul. 18, 2003, pp. 249-259.
Rodriguez-Fuentes, et al., "Enterex: Anti-diarrheic drug based on purified natural clinoptilolite," Zeolites, vol. 19, 1997, pp. 441-448.
Cerri, et al., "Zeolites in Biomedical Application: Zn-exchanged clinoptilolite-rich rock as active carrier for antibiotics in anti-acne topical therapy," Applied Clay Science, Elsevier Science, NL, vol. 27, No. 3-4, Dec. 2004, pp. 141-150.
Grce, et al., "Antiviral Properties of Clinoptilolite," Microporous and Mesoporous Materials, Elsevier Science Publishing, New York, US, vol. 79, No. 1-3, Apr. 1, 2005, pp. 165-169.
Faghihian, et al., "Adsorption of chromate by clinoptilolite exchanged with various metal catons," Water Research, Elsevir, Amsterdam, NL, vol. 39, No. 6, Mar. 2005, pp. 1099-1104.
Sprynskyy,et al., "Ammonium sorption from aqueous solutions by the natural zeolite Transcarpathian clinoptilolite studied under dynamic conditions," Journal of Colloid and Interface Science, Academic Press, New York, US, vol. 284, No. 2, Apr. 15, 2005, pp. 408-415.
Sprynskyy,et al., "Study of the selection mechanism of heavy metal ($Pb^{2+}$, $Cu^{2+}$, $Ni^{2+}$, and $Cd^{2+}$) adsorption on clinoptilolite," Journal of Colloid and Interface Science, vol. 304, No. 1, Dec. 1, 2006, pp. 21-28.
International Search Report and Written Opinion issued in International Patent Application No. PCT/IB2006/053178 dated Jun. 11, 2007.

* cited by examiner

*Primary Examiner* — Anoop Singh
*Assistant Examiner* — Anna Falkowitz
(74) *Attorney, Agent, or Firm* — Grossman Tucker Perreault & Pfleger PLLC

(57) ABSTRACT

The invention is for a method of potentiating clinoptilolite, the method including the steps of: providing fresh or spent clinoptilolite; exposing the clinoptilolite to a saline solution having a sodium ion content of about 10% to liberate impurities from the clinoptilolite; and drying the washed clinoptilolite fraction to render a potentiated clinoptilolite fraction. Preferably, the clinoptilolite is exposed to the saline solution for a period of about 48 hours. The washed clinoptilolite may be dried by filtered, heated air. This allows an optimal cation exchange capacity of the clinoptilolite to be reached. The clinoptilolite has uses as a medicament for a variety of aliments.

21 Claims, 4 Drawing Sheets

Graph 1. Preventative assessment: Stool weights after induction of diarrhoea

Graph 2. Preventative assessment: Net stool weight

Graph 3. Preventative assessment: Frequency of defecation after the induction of diarrhoea Graph 4. Preventative assessment: Net defecation frequency Graph 7. Curative assessment: Frequency of defecation after the induction of diarrhoea Graph 8. Curative assessment: Net defecation frequency $* P < 0.05$

PHARMACEUTICAL COMPOSITION INCLUDING CLINOPTILOLITE

FIELD OF THE INVENTION

THIS INVENTION relates to a pharmaceutical composition which includes clinoptilolite, as well as to a method of enhancing the efficacy of clinoptilolite in sequestering harmful compounds. More specifically, the invention relates to the use of potentiated clinoptilolite in treating various medical conditions.

BACKGROUND TO THE INVENTION

Zeolites are a group of naturally occurring and synthetic microporous, crystalline, hydrated aluminosilicates. Zeolites have well defined chemical structures containing $AlO_4$ and $SiO_4$ moieties linked through a common oxygen atom. The Applicant is aware of many uses of zeolites in both industry and agriculture which is due to their three-dimensional structure, which endows them with specific physicochemical properties including: ion exchange capacity, adsorbent nature, size exclusion framework as well as catalytic properties.

Clinoptilolite, colloquially known as clinoptolite, is a geological term used to describe one of the naturally occurring, high silica content zeolites. The functional physicochemical attributes of clinoptilolite in its natural state allow for its usage in many applications such as in chemical sieve applications, gas adsorption applications, as feed additives, as food additives, odour control agents, and as a water filter for municipal and residential drinking water.

Additionally, clinoptilolite in its natural state is known to exhibit diverse biological activities and may be of clinical use as an adjuvant to anticancer therapy, as a vaccine adjuvant, as a glucose adsorbent for the treatment of diabetes, as an antioxidant, and as a regulator of the immune system.

Clinoptilolite in its naturally occurring state is not always Ideal for use as an adsorption, sieving or sequestering agent, as it frequently has varying amounts of contaminants associated therewith which tend to impede the adsorptive, sieving and/or sequestering capabilities thereof. Such contaminants also tend to impede the cation exchange capabilities of naturally occurring clinoptilolite.

It is an object of this invention to potentiate clinoptilolite in order to increase the adsorptive, sieving, sequestering, and/or cation exchange capabilities of naturally occurring clinoptilolite.

SUMMARY OF THE INVENTION

According to one aspect of the invention, there is provided a method of potentiating clinoptilolite, the method including the steps of:

providing fresh or spent clinoptilolite;

exposing the clinoptilolite to a saline solution having a sodium ion content of between 0.1% and 60% to liberate impurities from the clinoptilolite; and drying the washed clinoptilolite fraction to render a potentiated clinoptilolite fraction.

The clinoptilolite may be exposed to the saline solution for a period of between 0.1 hours and 100 days, preferably between 12 hours and 72 hours. Most preferably, the clinoptilolite is exposed to the saline solution for a period of about 48 hours. This allows an optimal cation exchange capacity of the clinoptilolite to be reached.

The saline solution may, in a preferred embodiment, have a sodium ion content of between 5% and 20%, most preferably about 10%.

The clinoptilolite may be exposed to the saline solution in a ratio of between 1:1 and 1:100 clinoptilolite:saline solution, preferably between 1:1 and 1:10.

The washed clinoptilolite may be dried by filtered, heated air. The air may be heated to a temperature of between 40° C. and 450° C., preferably between 80° C. and 120° C., most preferably about 100° C.

Typically, drying may occur in an encapsulated or sealed liquidized bed reactor. Alternatively, drying may also be accomplished under a vacuum, which the Applicant has found increases the cationic exchange capacity of the clinoptolite.

The clinoptilolite may be ground to produce particles having an average particle size of between 0.1 μm and 3 mm, depending on the intended use of the clinoptilolite. The potentiated clinoptilolite may comprise particles with an average particle size of less than 2 mm, preferably less than 1.8 mm, more preferably less than 1 mm, typically between 0.1 mm and 1 mm, e.g. about 0.5 mm.

It is to be understood that the smaller the average size of the clinoptilolite particles, the larger the available reaction surface is per particle for reacting with compounds which are to be adsorbed or sequestered by the clinoptilolite.

The clinoptilolite may be bulked in bags prior to washing. Fortuitously, the method of the invention allows clinoptilolite to be processed in bulk, by allowing bags to be processed in large holding baths, typically 20 ton holding baths.

Following washing, the clinoptilolite may be briefly rinsed with water to remove excess sodium, prior to drying thereof.

According to another aspect of the invention, there is provided a pharmaceutical composition or medicament which includes potentiated clinoptilolite produced using the method of the invention.

According to yet another aspect of the invention, there is provided the use of potentiated clinoptilolite produced using the method of the invention, for the manufacture of a pharmaceutical composition or for preparing a medicament.

Another aspect of the invention provides a method of treating renal disease caused by increased amounts of nitrates or toxins in the kidneys, the method including the steps of bypassing the renal artery, introducing a suspension containing the potentiated clinoptilolite of the invention into the kidneys via the renal artery and, after a suitable residence time in the kidneys, removing the spent clinoptilolite from the kidneys via the renal vein, thereby reducing the amount of nitrates and toxins in the kidneys.

The medicament or pharmaceutical composition may be used for treating a condition selected from the group consisting of medication overdose, heavy metals poisoning, nitrates poisoning, alcohol poisoning, alcoholic keto-acidosis, Alzheimer's disease, cancer, diabetes, diarrhoea, fungal infection, bacterial infection, gastrointestinal disease, gout, gout caused by cytotoxic chemotherapy, heartburn, diabetic keto-acidosis, kidney stones, uric acid stones, osteoporosis, Parkinson's disease, haemochromatosis, peptic ulcers, viral infection, high cholesterol, and calcium and magnesium shortage.

According to a still further aspect of the invention, there is provided a substance or composition for use in a method of treatment of a condition selected from the group consisting of medication overdose, heavy metals poisoning, nitrates poisoning, alcohol poisoning, alcoholic keto-acidosis, Alzheimer's disease, cancer, diabetes, diarrhoea, fungal infection, bacterial infection, gastrointestinal disease, gout, gout caused by cytotoxic chemotherapy, heartburn, diabetic keto-acidosis, kidney stones, uric acid stones, osteoporosis, Parkinson's disease, haemochromatosis, peptic ulcers, viral infection, high cholesterol, and calcium and magnesium shortage, said substance or composition including clinoptilolite potentiated using the method of the invention to improve or change or enhance the cation exchange capacity of the clinoptilolite and said method including administering an effective dose of the substance or composition to a patient in need thereof.

According to another aspect of the invention, there is provided a method of treating a patient suffering from a condition selected from the group consisting of medication overdose, heavy metals poisoning, nitrates poisoning, alcohol poisoning, alcoholic keto-acidosis, Alzheimer's disease, cancer, diabetes, diarrhoea, fungal infection, bacterial infection, gastrointestinal disease, gout, gout caused by cytotoxic chemotherapy, heartburn, diabetic keto-acidosis, kidney stones, uric acid stones, osteoporosis, Parkinson's disease, haemochromatosis, peptic ulcers, viral infection, high cholesterol, and calcium and magnesium shortage, the method including administering an effective amount of potentiated clinoptilolite which has been potentiated by the method of the invention to change or enhance the cation exchange capacity of the clinoptilolite, to the patient.

The viral infection may be caused by an adenovirus, a herpesvirus, or an enterovirus, e.g. coxsackievirus, echovirus or rotavirus.

The potentiated clinoptilolite of the invention also has a use as an adjuvant to anticancer therapy, a vaccine adjuvant, or as a glucose adsorbent, useful for the treatment of diabetes.

The method typically includes administering the clinoptilolite orally, e.g. in the form of a suspension in water.

The medicament or pharmaceutical composition may also be used for adsorption or sequestration of toxins, metals and/or nitrates in a human or animal body, for calcium and magnesium supplementation, to increase the red blood cell count in the human or animal body, or to remove odours from the human or animal body, e.g. to treat halitosis or by absorbing excess ammonia or urates.

According to yet a further aspect of the invention, there is provided a method of treating a human or animal body to remove metals and/or nitrates therefrom, which includes orally administering to a human or animal an effective quantity of potentiated clinoptilolite produced using the method of the invention, and allowing the potentiated clinoptilolite to adsorb metals and/or nitrates from linings of the alimentary canal or digestive tract while in contact with these linings.

The alimentary canal or digestive tract of the human body includes the mouth, pharynx, esophagus, stomach and intestine. While many substances, such as metals and nitrates, can be absorbed from any part of the alimentary canal, it is believed that excess amounts of these substances, which can function as impurities or toxins to the body when present in excess amounts, will in particular be absorbed from the linings of the stomach and intestine.

The potentiated clinoptilolite, when in contact with linings of the alimentary canal, adsorbs substances, such as metals, particularly metals such as Pb, Cs, Rb, K, Ba, Sr, Zn, Cu, Co, Ni, Hg, Fe, Al, and Li, and nitrates, while at the same time releasing calcium and magnesium, which can be beneficial to the human or animal body.

The substances, such as metals and/or nitrates, which are adsorbed to or sequestered by the potentiated clinoptilolite, are removed from the body during faecal passage.

The clinoptilolite may be administered at a dosage rate of between 100 mg and 6 g per dose, typically once to three times daily. In a preferred embodiment of the invention, the clinoptilolite may be administered at a dosage rate of about 1.5 g, twice daily.

The potentiated clinoptilolite may be administered in the form of a suspension in a liquid, such as water. Preferably, the potentiated clinoptilolite is in particulate form, although it may also be in the form of a tablet or capsule.

According to yet a further aspect of the invention, there is provided the use of potentiated clinoptilolite capable of absorbing metals and/or nitrates, in the manufacture of a medicament to treat excessive levels of metals and/or nitrates in a human or animal body by oral ingestion thereof.

According to yet another aspect of the invention, there is provided a skin scrub, facial scrub, topical ointment, or adsorbent for topical application having included therein potentiated clinoptilolite produced using the method of the invention, and a suitable carrier.

The term "potentiated clinoptilolite" is meant to indicate clinoptilolite produced using the method of the invention, as described hereinbefore.

The invention will now be described in more detail with reference to the following non-limiting examples and drawings.

DRAWINGS

DETAILED DESCRIPTION OF THE INVENTION

Figure 1:
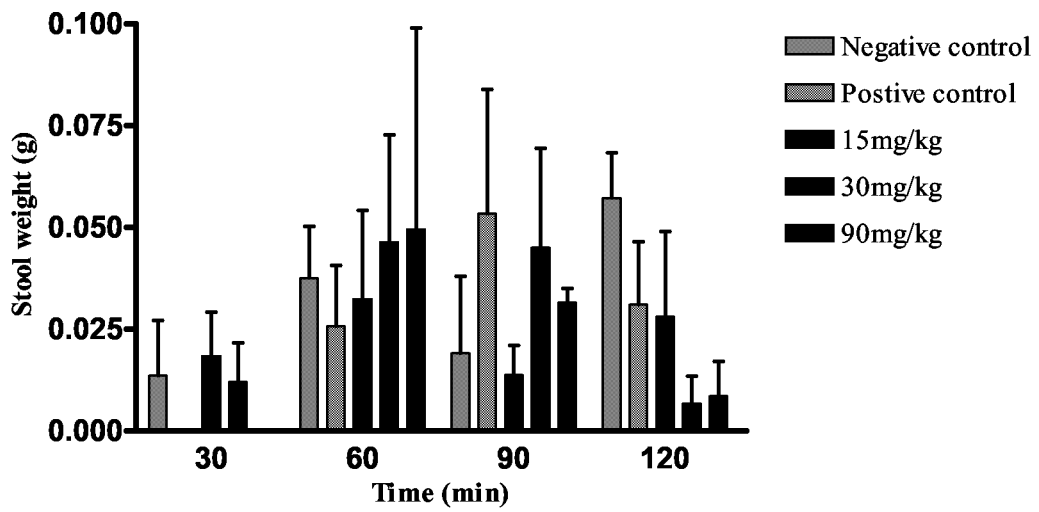
FIG. 1 shows stool weights after induction when conducting an assessment of the use of clinoptilolite in ameliorating diarrhoea preventatively.

It has been shown previously that oral administration of clinoptilolite to mice and rats for between 6 and 12 months shows no toxicity. In addition, when clinoptilolite was given to rats and dogs displaying a variety of different cancers, certain cancers where shown to shrink and an improvement in overall health status of some animals and prolongation of life was observed. It has also been shown that the intestinal system's proteolytic capacity and disacaridase potential are not modified through clinoptilolite administration.

Example 1

Analysis of Potentiated Clinoptilolite

The raw clinoptilolite which is the subject matter of this invention is available locally in South Africa and comprises 80% to 85% (by mass) clinoptilolite with the balance being primarily opaline cristobalite, K-feldspar and traces of sanidine (montmorillonite and quartz).

| The chemical analysis of a typical clinoptilolite sample is as follows: | |
|---|---|
| Substance | Mass % |
| $SiO_2$ | 71.52 |
| $Al_2O_3$ | 12.10 |
| $Na_2O$ | 1.40 |
| $K_2O$ | 3.85 |
| MgO | 0.86 |
| CaO | 1.53 |
| $Fe_2O_3$ | 1.21 |
| $TiO_2$ | 0.13 |
| MnO | 0.07 |
| Cu | Trace |
| Co | Nil |
| P | 0.009 |
| Ni | Trace |
| Cr | Trace |
| Ba | Trace |
| Sr | Trace |
| Total Water | 7.30 |
| Free Water | 5.7 |

In one embodiment of the invention, clinoptilolite is potentiated by providing fresh or spent clinoptilolite, and exposing the clinoptilolite to a saline solution having a sodium ion content of about 10% to liberate impurities from the clinoptilolite. The clinoptilolite is rinsed briefly with water to rid the clinoptilolite of excess saline, following which the clinoptilolite is dried in a sealable liquidized bed reactor at a temperature of 100° C. until sufficiently dry. The air used in drying the clinoptilolite is passed through filters in order to rid the air of impurities. Drying may occur in an encapsulated or sealed liquidized bed reactor, alternatively under vacuum conditions. The Applicant has found, after much experimentation, that vacuum drying is particularly beneficial for potentiating the clinoptilolite, as it increases the cation exchange capacity thereof. Using the washing and vacuum drying method of the invention, the cation exchange capacity of the clinoptilolite may be increased to as much as 4.2 meq/g.

Typically, the clinoptilolite is washed in or exposed to the saline solution for a period of about 48 hours, which allows an optimal cation exchange capacity of the clinoptilolite to be reached. The clinoptilolite is washed in or exposed to the saline solution in a ratio of about 1:10 clinoptilolite:saline solution in a particular embodiment of the invention.

Prior to washing the clinoptilolite, rough clinoptilolite is ground to produce particles having an average particle size of between 0.5 mm, but this may vary depending on the intended use of the clinoptilolite. It is to be understood that the smaller the average size of the clinoptilolite particles, the larger the available reaction surface is per particle for reacting with compounds which are to be adsorbed or sequestered by the clinoptilolite.

The clinoptilolite is packed in bulk bags prior to washing. Using the method of the invention, the clinoptilolite can easily be processed in bulk, by allowing large bluk bags containing clinoptilolite to be processed in large holding baths, typically 20 ton holding baths.

After heat treatment, the cation exchange capacity of the clinoptilolite has a theoretical maximum of 2.2 meq/g with its practical maximum being 1.8 meq/g. In addition to being able to absorb metals and nitrates, it can also absorb gases such as $NH_3$, $SO_2$, $CO_2$, Ar, and $N_2$. Its selectivity in respect of exchange of ions is as follows: Pb>Cs>Rb>K>$NH_4$>Ba>Sr>Pb>Zn>Cu>Co>Ni>Hg>Na>Ca>Fe>Al>Mg>Li.

| Its physical properties are as follows: | |
|---|---|
| Property | Value |
| Refractive index | 1.484 |
| Specific gravity | 2.2 g/cm³ |
| Bulk density | 1.92 g/cm³ |

Example 2

Adsorption Behaviour

The adsorption behaviour of potentiated clinoptilolite with respect to $Co^{2+}$, $Cu^{2+}$, $Zn^{2+}$ and $Mn^{2+}$ was studied in order to consider its application in the treatment of wastewaters. A batch method was employed, using metal concentrations in solution ranging from 100 to 400 mg per liter. The percentage adsorption and distribution coefficients ($K_d$) were determined for the adsorption system as a function of sorbent concentration. It was found that, in every concentration range, adsorption ratios of potentiated clinoptilolite metal cations matched to Langmuir, Freundich and Dubinin-Kaganer-Radushkevich (DKR) adsorption isotherm data. It was found that the adsorption phenomena depend on charge density and hydrated ion diameter. According to these equilibrium studies, the selectivity sequence of potentiated clinoptilolite can be given as $Co^{2+}>Cu^{2+}>Zn^{2+}>Mn^{2+}$.

Clinoptilolite can be administered orally at a dosage rate of 100 mg to 6 g, as tablets or capsules, or as a suspension in water. When consumed orally in this fashion on a daily basis, the clinoptilolite absorbs toxins or other unwanted substances, such as heavy metals and nitrates, continuously from the linings of the alimentary canal, as hereinbefore described, so that the likelihood of build-up of such heavy metals and nitrates to a level at which they can constitute impurities or toxins is thus reduced. It is expected that ailments or conditions such as medication overdose, heavy metals poisoning, nitrates poisoning, alcohol poisoning, alcoholic keto-acidosis, Alzheimer's disease, cancer, diabetes, diarrhoea, fungal infection, bacterial infection, gastrointestinal disease, gout, gout caused by cytotoxic chemotherapy, heartburn, diabetic keto-acidosis, kidney stones, uric acid stones, osteoporosis, Parkinson's disease, haemochromatosis, peptic ulcers, viral infection, high cholesterol, and calcium and magnesium shortage can be reduced or treated by regularly consuming clinoptilolite in accordance with the invention.

In addition, the clinoptilolite of the invention also has a particularly beneficial use in the following areas: as adjuvant to anticancer therapy, as a vaccine adjuvant, and as glucose adsorbent for the treatment of diabetes.

Clinoptilolite stabilizes and regulates the digestive system, along with elimination of and recuperation from damage or disturbances to the digestive system such as heartburn, stomach and duodenal ulcers, which is shown in greater detail below.

Example 3

Antidiarrhoeal Properties

Animals

Thirty, same aged, laboratory bred, female, NMRI mice (average body weight, 28 g) were individually housed in appropriate cages and kept in a controlled room. All the animals were provided food (standard laboratory pellets) and water ad libitum. The mice underwent a period of acclimatization to the laboratory conditions for 7 days before onset of experimentation. The mice were randomly assigned to either the preventative or the curative assessment. After completion of experimentation all the animals were terminated through $CO_2$ asphyxiation.

Murine Enterotoxin-Induced Diaffhoea Model

Diarrhoea was induced in all the mice by oral administration of E. coli-sta enterotoxin [70 μg/kg] made up in a 0.2 ml volume of saline solution. The anti-diarrhoeal potential of clinoptilolite of the invention was assessed from both a preventative and a curative viewpoint:

Preventative Assessment

Non-fasted mice (n=15) were divided equally into five groups of three each.

The following was administered orally via gavage to the respective groups:
  Group 1, the negative control, received 0.2 ml of saline solution.
  Group 2, the positive control, received loperamide-HCL [2 mg/kg] in 0.2 ml saline.
  Group 3, received clinoptilolite of the invention [15 mg/kg] in 0.2 ml of saline solution.
  Group 4, received clinoptilolite of the invention [30 mg/kg] in 0.2 ml of saline solution.
  Group 5, received clinoptilolite of the invention [90 mg/kg] in 0.2 ml of saline solution.

After 50 min, diarrhoea was induced in all animals. Thereafter, every 30 min for a period of 2 hours, the faeces of each animal was individually collected in order to determine the frequency and weight thereof.

Curative Assessment

Non-fasted mice (n=15) were divided equally into five groups of three each.

Diarrhoea was first induced. Thirty minutes thereafter, the following was administered orally via gavage to the respective groups:
  Group 1, the negative control, received 0.2 ml of saline solution.
  Group 2, the positive control, received loperamide HCL [2 mg/kg] in 0.2 ml saline.
  Group 3, received clinoptilolite of the invention [15 mg/kg] in 0.2 ml of saline solution.
  Group 4, received clinoptilolite of the invention [30 mg/kg] in 0.2 ml of saline solution.
  Group 5, received clinoptilolite of the invention [90 mg/kg] in 0.2 ml of saline solution.

After induction of diarrhoea every 30 min for a period of 2 hours, the faeces of each animal was individually collected in order to determine the frequency and weight.

Results

Results are expressed for each of the two assessments are shown as graphs in FIGS. 1 to 8.

Conclusions

The methods used to induce diarrhoea did not result in watery, unformed stools—the consistency of collected stools did not appear changed after diarrhoea had been induced. The frequency and net faecal output in terms of weight did appear to be increased and this could be reduced in certain instances significantly by the respective treatments.

Figure 2:
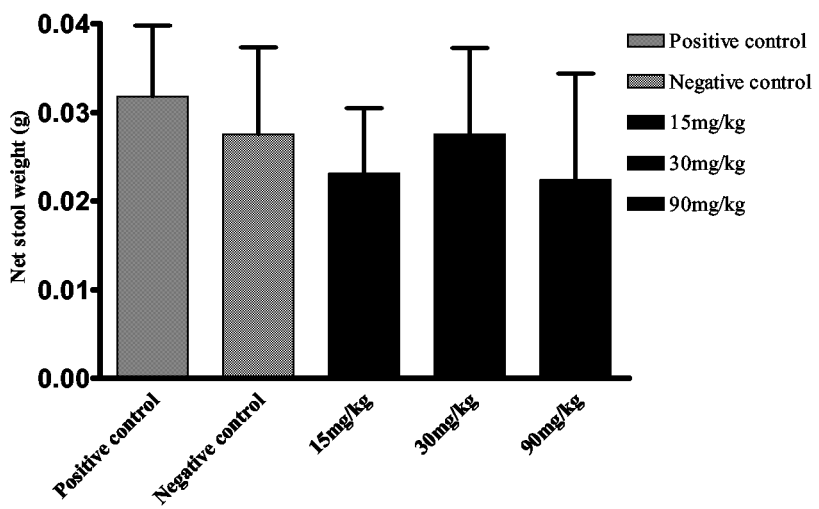
FIG. 2 shows net stool weights when conducting an assessment of the use of clinoptilolite in ameliorating diarrhoea preventatively.
Figure 3:
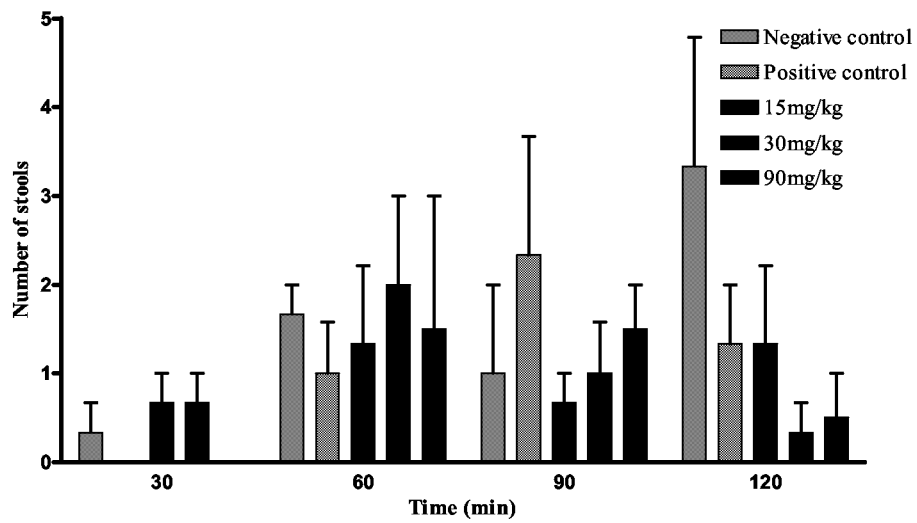
FIG. 3 shows frequency of defection after the induction of diarrhoea when conducting an assessment of the use of clinoptilolite in ameliorating diarrhoea preventatively.
Figure 4:
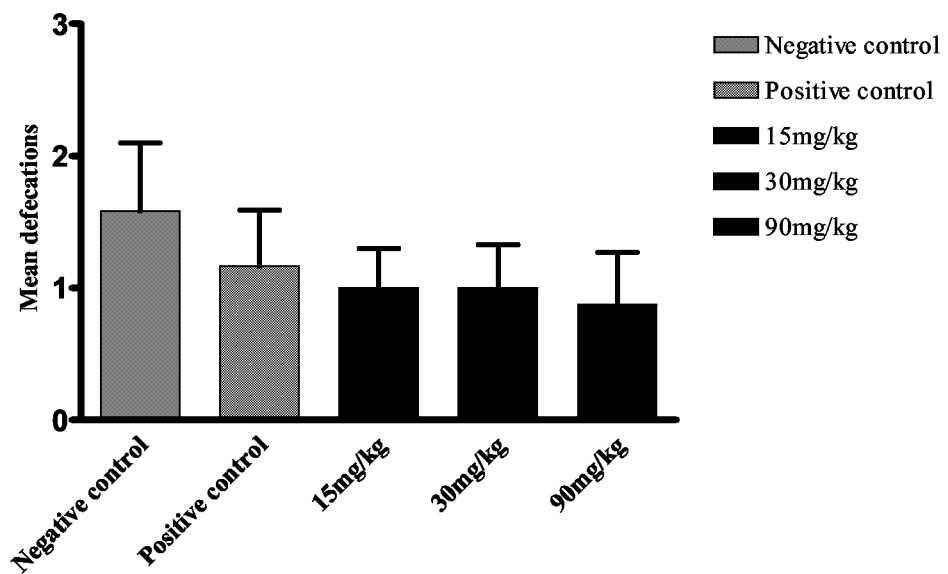
FIG. 4 shows net defecation frequency when conducting an assessment of the use of clinoptilolite in ameliorating diarrhoea preventatively.
Figure 5:
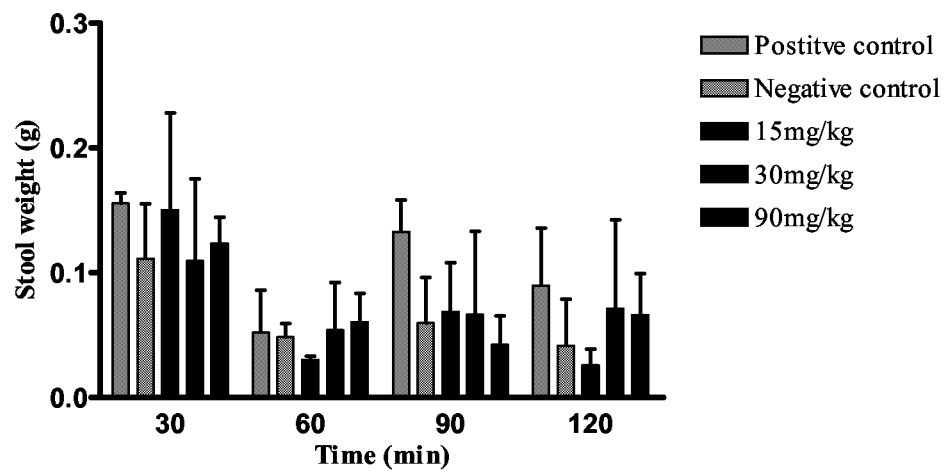
FIG. 5 shows stool weights after induction when conducting an assessment of the use of clinoptilolite in ameliorating diarrhoea curatively.

From a preventative view point, FIGS. 2 and 4 display that over the full period of observation, both the positive control and the potentiated clinoptilolite treatment groups resulted in a reduction in both net stool weight and mean number of stools passed as compared to the negative control.

Figure 6:
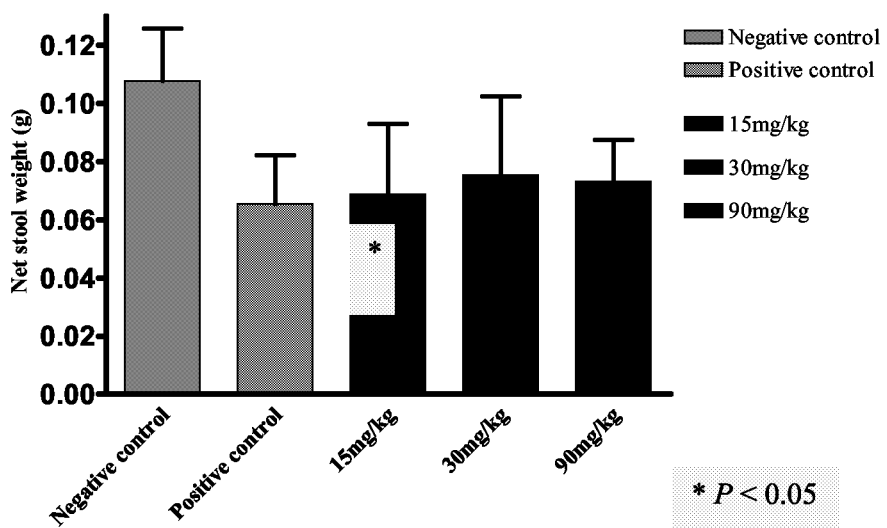
FIG. 6 shows net stool weights when conducting an assessment of the use of clinoptilolite in ameliorating diarrhoea curatively.
Figure 7:
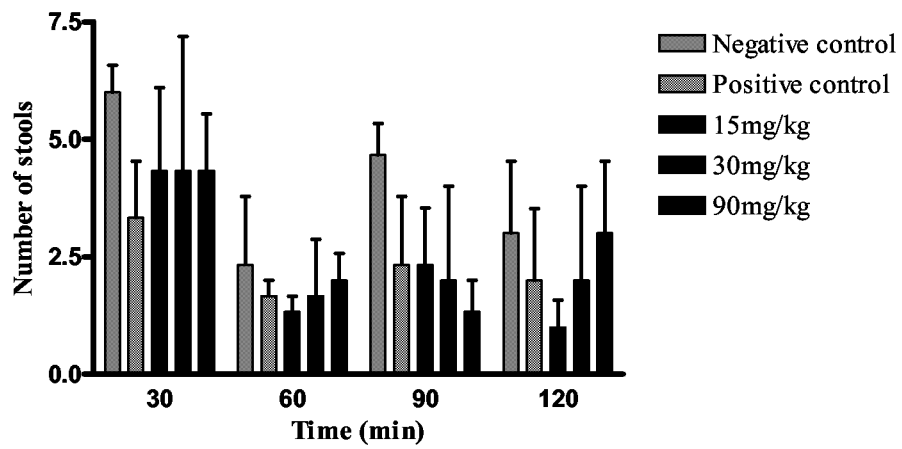
FIG. 7 shows frequency of defecation after the induction of diarrhoea when conducting an assessment of the use of clinoptilolite in ameliorating diarrhoea curatively.
Figure 8:
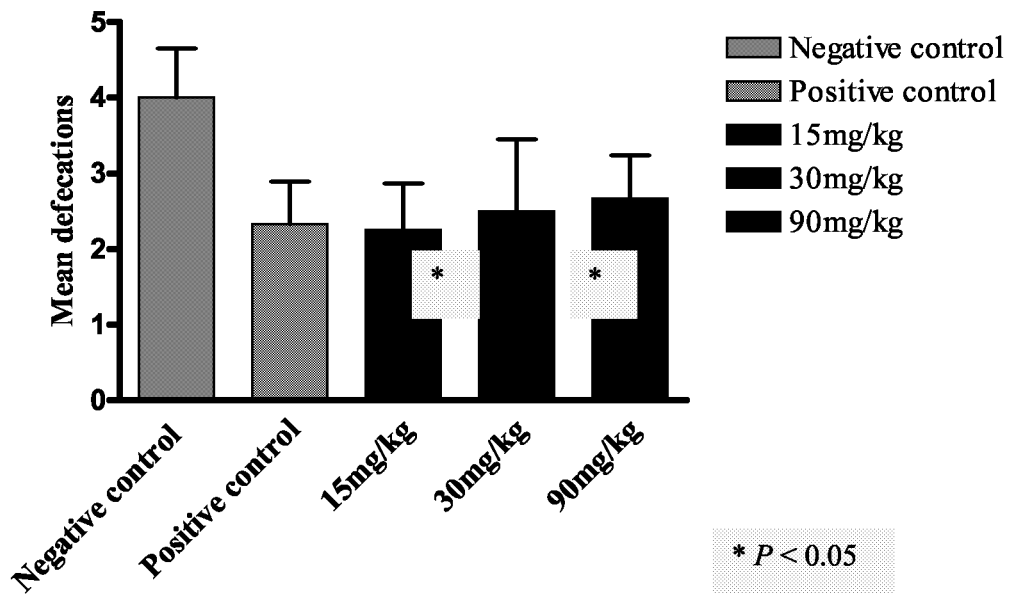
FIG. 8 shows net defecation frequency when conducting an assessment of the use of clinoptilolite in ameliorating diarrhoea curtively.

From a curative view-point, FIGS. 6 and 8 show that both net stool weight and mean number of stools was drastically reduced as compared to the negative control:

The reduction in stool weight by the positive control, loperamide (FIG. 6), was shown to be significant ($P<0.05$) as compared to the negative control.

Additionally the frequency of defecation was shown to be significantly reduced ($P<0.05$) as compared to the saline treated negative control by both the loperamide and the [15 mg/kg] potentiated clinoptilolite treatment group (FIG. 8).

Example 4

Heartburn Relief

Study Objectives
  To evaluate the effectiveness of clinoptilolite of the invention to relieve heartburn in patients suffering from endoscopic negative GORD through measurement of symptom-free days and patients' experience of heartburn and discomfort.
  To evaluate if the clinoptilolite of the invention can improve quality of life in patients suffering from heartburn.
  To evaluate if the clinoptilolite of the invention can reduce the frequency of rescue medication use.

Materials and Methods

A double blind, placebo controlled trial, with randomization to trial treatment into one of the two treatment arms was performed. Patients were randomized to receive either a placebo or the clinoptilolite of the invention as 750 mg capsule, three times daily for a period of 14 days by means of a computer generated randomization list.

Patients were assessed on use of rescue medication, symptom-free days and evaluation of quality of life by means of questionnaires. Rescue medication, PPI, (Nexiamo 20 mg) was part of on-demand therapy for all the patients. Patients between the ages of 18-85 years were included in the trial if they were diagnosed with ENGORD, were otherwise healthy and signed informed consent.

Patient Randomization

The study involved 25 patients. Thirteen patients were randomized to received the clinoptilolite of the invention and twelve to receive a placebo. A total of five patients did not complete the study successfully; three patients did not return on scheduled visits with no reported side-effects (2 received placebo, 1 the clinoptilolite of the invention). One serious adverse event and one adverse event were reported (see Table 2 below).

Results

The pilot study measured several outcomes. All data was analyzed by means of an unpaired t-test, 95% confidence interval. Data was considered significant at a p-value<0.05. The data set was analyzed using a software program, FIGUREPAD, and results are tabulated in Table 1. Patients receiving the clinoptilolite of the invention indicated an overall improvement of approximate 50% in several of the study outcomes. Discomfort clinically improved by (48%), pain (49%), symptom-free days improved by 31% and total heartburn episodes per day decreased by 44% when the clinoptilolite of the invention was compared to the placebo group. Although the use of rescue medication in the placebo group was slightly lower than in the group receiving the clinoptilolite of the invention, this was not significant.

TABLE 1

Summary of the results on the study outcomes

| Event | Placebo n = 10 | Clinoptilolite n = 10 | 95% CI (p = 0.05) |
|---|---|---|---|
| Pain | 1.841 ± 1.355 | 0.903 ± 0.671 | 0.065 |
| Discomfort | 2.534 ± 0.396 | 1.213 ± 0.270 | 0.013 |
| Heartburn episodes | 1.384 ± 0.309 (52%) | 0871 ± 0.215 (29%) | 0.190 |
| Symptom-free days | 40/140 (29%) | 59/140 (42%) | |
| Use of rescue medication | 13/140 (9%) | 29/140 (21%) | NS |

TABLE 2

Reported side-effects

| Symptom | Clinoptilolite n = 10 | Placebo n = 10 |
|---|---|---|
| Constipation | 2/10 | 0/10 |
| Bloatedness | 3/10 | 0/10 |
| Nausea | 1/10 | 1/10 |
| Sleeplessness | 1/10 | 0/10 |
| No side-effects | 4/10 | 9/10 |

Conclusion

This study indicates the use of the clinoptilolite of the invention in the treatment of non-complicated GORD. Results obtained from this study indicate overall clinical improvement, up to 50%, in several of the study outcome groups.

Without wishing to be bound by theory, the Applicant believes that the clinoptilolite functions as a molecular sieve and that the heat treatment and salinization of the clinoptilolite increases the molecular sieve apertures. By carefully controlling the heat treatment of the clinoptilolite, the molecular sieve aperture size can be selected and controlled to allow the molecular sieve to be configured or adapted to absorb a cation or cations of particular size by way of cation exchange.

Example 5

Antidiarrhoeal Properties

Animals

Thirty, female NMRI mice (25-35 g, body weight) were procured from the National Health Laboratory Services (NHLS) in South Africa. The total duration of the study was 2 days. Only young healthy animals with no skin lesions were admitted to the study. A veterinarian confirmed the health status of the animals. No animals were withdrawn from the study.

Housing

The mice were acclimatized in the animal unit of La-Bio Research for a period of 7 days before the start of the study at a room temperature of between 19-23° C. and a humidity of 45-60%. A 12-hour lightnight cycle was kept constant in the animal unit. The light intensity was kept between 70-100 Lux. The animals were kept in a micro-barrier unit consisting out of individually ventilated cages. One mouse was kept per cage. The physical size of the cages was in accordance with European standards. Water, food and bedding was autoclaved. Ratmice feed was in the form of pellets procured from EPOL South Africa. Food was not withheld at any stage of the study from the animals. The bedding material, Vermiculite, was obtained from an ISO 2000 accredited supplier. Water was available ad libitum to the animals. The water, food and bedding were inspected every day and replaced when necessary. No medication or vaccination of the animals was done.

Experimental Design

Diarrhoea was induced in all mice (experimental and control) by oral administration of $E.\ coli$-sta enterotoxin [70 µg/kg] made up in a 0.2 ml volume of saline solution.

Assessment of Preventative Use of Potentiated Clinoptilolite

Non-fasted mice (n^IS) were divided equally into 5 groups of 3. The following was administered orally via gavage to the respective groups:

Group 1, the negative control, received 0.2 ml of saline solution;

Group 2, the positive control, received loperamide HCL [2 mg/kg] in 0.2 ml saline;

Group 3 received potentiated clinoptilolite of the invention (termed "Absorbatox" in this range of experiments) [15 mg/kg] in 0.2 ml of saline solution;

Group 4 received potentiated clinoptilolite of the invention [30 mg/kg] in 0.2 ml of saline solution;

Group 5 received potentiated clinoptilolite of the invention [90 mg/kg] in 0.2 ml of saline solution.

The mice in each of the groups received an oral dose of $E.\ coli$-sta enterotoxin [70 µg/kg] made up in a 0.2 ml volume of saline solution after being dosed with the above mentioned test materials.

After 60 minutes, the faeces of each animal was individually collected and weighed every 30 min for a period of 120 min.

Assessment of Curative Use of Potentiated Clinoptilolite

Non-fasted mice (n=15) were divided equally into 5 groups of 3. The mice in each of the groups received an oral dose of $E.\ coli$-sta enterotoxin [70 µg/kg] made up in a 0.2 ml volume of saline solution before receiving the curative treatments.

Thirty minutes thereafter, the following was administered orally via gavage to the respective groups:

Group 1, the negative control, received 0.2 ml of saline solution;

Group 2, the positive control, received loperamide HCL [2 mg/kg] in 0.2 ml saline;

Group 3 received potentiated clinoptilolite of the invention (termed "Absorbatox" in this range of experiments) [15 mg/kg] in 0.2 ml of saline solution;

Group 4 received potentiated clinoptilolite of the invention [30 mg/kg] in 0.2 ml of saline solution;

Group 5 received potentiated clinoptilolite of the invention [90 mg/kg] in 0.2 ml of saline solution.

After induction of diarrhoea, the faeces of each animal was individually collected and weighed, every 30 min for a period of 120 min. All the mice were terminated using $CO_2$ at the end of the study.

Experimental Procedure

All mice were weighed one day before the initiation of the study. The bedding material were removed prior the dosage of each group and replaced after the documentation of the stool frequency of each mice as shown in study schedule. One day prior the study the dosages of both the medication and bacteria were prepared using the average weight of the 30 mice (28 g) supplied by the test laboratory. The first 15 mice were dosed (5 groups, 3 per group) on day 8. This was termed the preventative assessment. The last 15 mice were dosed (5 groups, 3 per group) on day 9. This was termed the curative assessment. The stool frequency and weight of mice in both the preventative and curative groups were recorded.

Observations

Each animal was observed after dosing. In this time, the frequency and net stool weight were determined for each animal. Any abnormal findings, including local, systemic and behavioural abnormalities were recorded. The stools of the mice were weighed every 30 minutes for 120 minutes.

Results

Preventative Assessment

TABLE 1

GROUP 1
Administer 0.2 ml saline solution via gavage to group 1: 8 h 00
Oral dose of *E. coli*-sta enterotoxin [70 ug/kg]: 9 h 00

|  | Time | Stool frequency | Stool weight |
|---|---|---|---|
| Animal 1 | 9 h 30 | 1 | 0.0405 g |
|  | 10 h 00 | 2 | 0.0620 g |
|  | 10 h 30 | 0 | 0 g |
|  | 11 h 00 | 1 | 0.03630 g |
| Animal 2 | 9 h 30 | 0 | 0 g |
|  | 10 h 00 | 1 | 0.019 g |
|  | 10 h 30 | 3 | 0.0576 g |
|  | 11 h 00 | 3 | 0.062 g |
| Animal 3 | 9 h 30 | 0 | 0 g |
|  | 10 h 00 | 2 | 0.0315 g |
|  | 10 h 30 | 0 | 0 g |
|  | 11 h 00 | 6 | 0.0735 g |

TABLE 2

The average weight and frequency of stool at the beginning and end of the observational period of group 1

| | |
|---|---|
| Average weight of stool at the beginning of observations | 0.0405 |
| Average weight of stool at the end of observations | 0.0572 |
| Average frequency of stool at the beginning of observations | 1 |
| Average frequency of stool at the end of observations | 3.3 |

TABLE 3

GROUP 2
Administer 2 mg/kg loperamide via gavage to group 2: 8 h 05
Oral dose of *E. coli*-sta enterotoxin [70 ug/kg]: 9 h 05

|  | Time | Stool frequency | Stool weight |
|---|---|---|---|
| Animal 4 | 9 h 35 | 0 | 0 g |
|  | 10 h 05 | 1 | 0.025 g |
|  | 10 h 35 | 5 | 0.114 g |
|  | 11 h 05 | 2 | 0.047 g |
| Animal 5 | 9 h 35 | 0 | 0 g |
|  | 10 h 05 | 0 | 0 g |
|  | 10 h 35 | 1 | 0.0209 g |
|  | 11 h 05 | 2 | 0.046 g |
| Animal 6 | 9 h 35 | 0 | 0 g |
|  | 10 h 05 | 2 | 0.052 g |
|  | 10 h 35 | 1 | 0.017 g |
|  | 11 h 05 | 0 | 0 g |

TABLE 4

The average weight and frequency of stool at the beginning and end of the observational period of group 2

| | |
|---|---|
| Average weight of stool at the beginning of observations | 0 |
| Average weight of stool at the end of observations | 0.031 |
| Average frequency of stool at the beginning of observations | 0 |
| Average frequency of stool at the end of observations | 1.3 |

TABLE 5

GROUP 3
Administer 15 mg/kg clinoptilolite via gavage to group 3: 8 h 10
Oral dose of *E. coli*-sta enterotoxin [70 ug/kg]: 9 h 10

|  | Time | Stool frequency | Stool weight |
|---|---|---|---|
| Animal 7 | 9 h 40 | 1 | 0.0175 g |
|  | 10 h 10 | 1 | 0.023 g |
|  | 10 h 40 | 0 | 0 g |
|  | 11 h 10 | 3 | 0.069 g |
| Animal 8 | 9 h 40 | 1 | 0.0375 g |
|  | 10 h 10 | 3 | 0.074 g |
|  | 10 h 40 | 1 | 0.025 g |
|  | 11 h 10 | 1 | 0.015 g |
| Animal 9 | 9 h 40 | 0 | 0 g |
|  | 10 h 10 | 0 | 0 g |
|  | 10 h 40 | 1 | 0.016 g |
|  | 11 h 10 | 0 | 0 g |

TABLE 6

The average weight and frequency of stool at the beginning and end of the observational period of group 3

| | |
|---|---|
| Average weight of stool at the beginning of observations | 0.018 |
| Average weight of stool at the end of observations | 0.028 |
| Average frequency of stool at the beginning of observations | 1 |
| Average frequency of stool at the end of observations | 1.3 |

TABLE 7

GROUP 4
Administer 30 mg/kg clinoptilolite via gavage to group 4: 8 h 20
Oral dose of *E. coli*-sta enterotoxin [70 ug/kg]: 9 h 20

|  | Time | Stool frequency | Stool weight |
|---|---|---|---|
| Animal 10 | 9 h 50 | 0 | 0 g |
|  | 10 h 20 | 3 | 0.099 g |
|  | 10 h 50 | 2 | 0.035 g |
|  | 11 h 20 | 1 | 0.017 g |
| Animal 11 | 9 h 50 | 0 | 0 g |
|  | 10 h 20 | 0 | 0 g |
|  | 10 h 50 | 1 | 0.028 g |
|  | 11 h 20 | 0 | 0 g |

TABLE 8

The average weight and frequency of stool at the beginning and end of the observational period of group 4

| | |
|---|---|
| Average weight of stool at the beginning of observations | 0 |
| Average weight of stool at the end of observations | 0.017 |
| Average frequency of stool at the beginning of observations | 0 |
| Average frequency of stool at the end of observations | 0.5 |

TABLE 9

GROUP 5
Administer 60 mg/kg clinoptilolite via gavage to group 5: 8 h 15
Oral dose of *E. coli*-sta enterotoxin [70 ug/kg]: 9 h 15

|  | Time | Stool frequency | Stool weight |
|---|---|---|---|
| Animal 13 | 9 h 45 | 1 | 0.0310 g |
|  | 10 h 15 | 3 | 0.091 g |
|  | 10 h 45 | 1 | 0.084 g |
|  | 11 h 15 | 0 | 0 g |

TABLE 9-continued

GROUP 5
Administer 60 mg/kg clinoptilolite via gavage to group 5: 8 h 15
Oral dose of *E. coli*-sta enterotoxin [70 ug/kg]: 9 h 15

|  | Time | Stool frequency | Stool weight |
|---|---|---|---|
| Animal 14 | 9 h 50 | 1 | 0.005 g |
|  | 10 h 20 | 0 | 0 g |
|  | 10 h 50 | 2 | 0.051 g |
|  | 11 h 20 | 1 | 0.02 g |
| Animal 15 | 9 h 50 | 0 | 0 g |
|  | 10 h 20 | 3 | 0.048 g |
|  | 10 h 50 | 0 | 0 g |
|  | 11 h 20 | 0 | 0 g |

TABLE 8

The average weight and frequency of stool at the beginning and end of the observational period of group 4

| | |
|---|---|
| Average weight of stool at the beginning of observations | 0.012 g |
| Average weight of stool at the end of observations | 0.02 g |
| Average frequency of stool at the beginning of observations | 1 g |
| Average frequency of stool at the end of observations | 0.5 |

Curative Assessment

TABLE 9

GROUP 1
Oral dose of *E. coli*-sta enterotoxin [70 ug/kg]: 8 h 30
Administer 0.2 ml saline solution via gavage to group 1: 9 h 00

|  | Time | Stool frequency | Stool weight |
|---|---|---|---|
| Animal 16 | 9 h 00 | 6 | 0.168 g |
|  | 9 h 30 | 2 | 0.042 g |
|  | 10 h 00 | 4 | 0.1186 g |
|  | 10 h 30 | 5 | 0.1601 g |
| Animal 17 | 9 h 00 | 5 | 0.140 g |
|  | 9 h 30 | 0 | 0 g |
|  | 10 h 00 | 6 | 0.1825 g |
|  | 10 h 30 | 4 | 0.1511 g |
| Animal 18 | 9 h 00 | 7 | 0.159 g |
|  | 9 h 30 | 5 | 0.115 g |
|  | 10 h 00 | 4 | 0.0978 g |
|  | 10 h 30 | 0 | 0 g |

TABLE 10

The average weight and frequency of stool at the beginning and end of the observational period of group 1

| | |
|---|---|
| Average weight of stool at the beginning of observations | 0.15 |
| Average weight of stool at the end of observations | 0.1 |
| Average frequency of stool at the beginning of observations | 6 |
| Average frequency of stool at the end of observations | 3 |

TABLE 11

GROUP 2
Oral dose of *E. coli*-sta enterotoxin [70 ug/kg]: 8 h 35
Administer 2 mg/kg loperamide via gavage to group 2: 9 h 05

|  | Time | Stool frequency | Stool weight |
|---|---|---|---|
| Animal 19 | 9 h 05 | 5 | 0.0940 g |
|  | 9 h 35 | 1 | 0.0418 g |
|  | 10 h 05 | 0 | 0 g |
|  | 10 h 35 | 0 | 0 g |

TABLE 11-continued

GROUP 2
Oral dose of *E. coli*-sta enterotoxin [70 ug/kg]: 8 h 35
Administer 2 mg/kg loperamide via gavage to group 2: 9 h 05

|  | Time | Stool frequency | Stool weight |
|---|---|---|---|
| Animal 20 | 9 h 05 | 4 | 0.195 g |
|  | 9 h 35 | 2 | 0.0247 g |
|  | 10 h 05 | 5 | 0.1256 g |
|  | 10 h 35 | 5 | 0.1160 g |
| Animal 21 | 9 h 05 | 1 | 0.045 g |
|  | 9 h 35 | 2 | 0.0664 g |
|  | 10 h 05 | 2 | 0.0541 g |
|  | 10 h 35 | 1 | 0.0092 g |

TABLE 12

The average weight and frequency of stool at the beginning and end of the observational period of group 2

| | |
|---|---|
| Average weight of stool at the beginning of observations | 0.012 |
| Average weight of stool at the end of observations | 0.02 |
| Average frequency of stool at the beginning of observations | 3.3 |
| Average frequency of stool at the end of observations | 2 |

TABLE 13

GROUP 3
Oral dose of *E. coli*-sta enterotoxin [70 ug/kg]: 8 h 40
Administer 15 mg/kg clinoptilolite via gavage to group 3: 9 h 10

|  | Time | Stool frequency | Stool weight |
|---|---|---|---|
| Animal 22 | 9 h 10 | 7 | 0.289 g |
|  | 9 h 40 | 1 | 0.0345 g |
|  | 10 h 10 | 3 | 0.1365 g |
|  | 10 h 40 | 1 | 0.0411 g |
| Animal 23 | 9 h 10 | 1 | 0.02 g |
|  | 9 h 40 | 2 | 0.0313 g |
|  | 10 h 10 | 4 | 0.0699 g |
|  | 10 h 40 | 2 | 0.0367 g |
| Animal 24 | 9 h 10 | 5 | 0.142 g |
|  | 9 h 40 | 1 | 0.0254 g |
|  | 10 h 10 | 0 | 0 g |
|  | 10 h 40 | 0 | 0 g |

TABLE 14

The average weight and frequency of stool at the beginning and end of the observational period of group 3

| | |
|---|---|
| Average weight of stool at the beginning of observations | 0.154 |
| Average weight of stool at the end of observations | 0.02 |
| Average frequency of stool at the beginning of observations | 4 |
| Average frequency of stool at the end of observations | 1 |

TABLE 15

GROUP 4
Oral dose of *E. coli*-sta enterotoxin [70 ug/kg]: 08 h 45
Administer 30 mg/kg clinoptilolite via gavage to group 4: 9 h 15

|  | Time | Stool frequency | Stool weight |
|---|---|---|---|
| Animal 25 | 9 h 15 | 2 | 0.068 g |
|  | 9 h 45 | 1 | 0.0341 g |
|  | 10 h 15 | 0 | 0 g |
|  | 10 h 45 | 0 | 0 g |

TABLE 15-continued

GROUP 4
Oral dose of *E. coli*-sta enterotoxin [70 ug/kg]: 08 h 45
Administer 30 mg/kg clinoptilolite via gavage to group 4: 9 h 15

|  | Time | Stool frequency | Stool weight |
|---|---|---|---|
| Animal 26 | 9 h 15 | 10 | 0.238 g |
|  | 9 h 45 | 4 | 0.1279 g |
|  | 10 h 15 | 6 | 0.2002 g |
|  | 10 h 45 | 6 | 0.3140 g |
| Animal 27 | 9 h 15 | 1 | 0.023 g |
|  | 9 h 45 | 0 | 0 g |
|  | 10 h 15 | 0 | 0 g |
|  | 10 h 45 | 0 | 0 g |

TABLE 16

The average weight and frequency of stool at the beginning
and end of the observational period of group 4

| Average weight of stool at the beginning of observations | 0.1 |
|---|---|
| Average weight of stool at the end of observations | 0.1 |
| Average frequency of stool at the beginning of observations | 4.3 |
| Average frequency of stool at the end of observations | 2 |

TABLE 17

GROUP 5
Oral dose of *E. coli*-sta enterotoxin [70 ug/kg]: 8 h 55
Administer 60 mg/kg clinoptilolite via gavage to group 5: 9 h 25

|  | Time | Stool frequency | Stool weight |
|---|---|---|---|
| Animal 28 | 9 h 25 | 5 | 0.165 g |
|  | 9 h 55 | 3 | 0.0938 g |
|  | 10 h 25 | 2 | 0.0787 g |
|  | 10 h 55 | 4 | 0.0949 g |
| Animal 29 | 9 h 25 | 2 | 0.096 g |
|  | 9 h 55 | 2 | 0.0711 g |
|  | 10 h 25 | 0 | 0 g |
|  | 10 h 55 | 0 | 0 g |
| Animal 30 | 9 h 25 | 6 | 0.11 g |
|  | 9 h 55 | 1 | 0.0167 g |
|  | 10 h 25 | 2 | 0.0491 g |
|  | 10 h 55 | 5 | 0.1036 g |

TABLE 18

The average weight and frequency of stool at the beginning
and end of the observational period of group 5

| Average weight of stool at the beginning of observations | 0.12 |
|---|---|
| Average weight of stool at the end of observations | 0.06 |
| Average frequency of stool at the beginning of observations | 4.3 |
| Average frequency of stool at the end of observations | 3 |

Example 6

Facial Scrub and Absorbent for Topical Applications

Protocol
Fifteen participatns were required to utilize a facial scrub containing the potentiated clinoptilolite for personal hygiene purposes for a period of 4 weeks in the same manner as their current scrub. Subjects were asked to score their general facial skin condition after using the potentiated clinoptilolite scrub compared to their regular facial scrub as follows:
1. Worse than current scrub
2. Similar to current scrub
3. Slight improvement over current scrub
4. Dramatic improvement over current scrub.
Results
Thirteen of the subjects indicated that they experience a dramatic improvement in facial skin condition using the potentiated clinoptilolite scrub of the invention, as compared to their current scrub, while two subjects indicated that they experienced no improvement.

The invention claimed is:

1. A method of removing at least one of metals and nitrates from a human or animal body, comprising:
    producing potentiated clinoptilolite by washing clinoptilolite in a saline solution having a sodium ion content ranging from about 0.1 to about 60 weight % and then vacuum drying the clinoptilolite at a temperature between 80° C. and 120° C., said potentiated clinoptilolite having a cation exchange capacity (CEC) exceeding 2.2 meq/g; and
    orally administering to said human or animal body an effective quantity of the potentiated clinoptilolite to remove at least one of metals and nitrates from said human or animal body.

2. The method of claim 1, wherein said potentiated clinoptilolite exhibits an ion exchange selectivity of Pb>Cs>Rb>K>NH4>Ba>Sr>Pb>Zn>Cu>Co>Ni>Hg>Na>Ca>Fe>Al>Mg>Li.

3. The method of claim 2, wherein said clinoptilolite is exposed to said saline solution for a period ranging from about 0.1 hours to about 100 days.

4. The method of claim 3, wherein said clinoptilolite is exposed to said saline solution for a period ranging from about 12 hours to about 72 hours.

5. The method of claim 4, wherein said clinoptilolite is exposed to said saline solution for a period of about 48 hours.

6. The method of claim 3, wherein said sodium ion content ranges from about 5 to about 20 weight %.

7. The method of claim 6, wherein said sodium ion content is about 10 weight %.

8. The method of claim 3, wherein said washing is performed using a ratio of clinoptilolite to saline solution ranging from about 1:1 to about 1:100.

9. The method of claim 8, wherein said washing is performed using a ratio of clinoptilolite to saline solution ranging from about 1:1 to about 1:10.

10. The method of claim 1, wherein said clinoptilolite is also dried with filtered air having a temperature ranging from about 40 to about 450° C.

11. The method of claim 10, wherein said filtered air has a temperature of about 100° C.

12. The method of claim 3, wherein said clinoptilolite has an average particle size ranging from about 0.1 μm to about 0.5 mm.

13. The method of claim 1, wherein said clinoptilolite has an average particle size ranging from about 0.2 μm to about 20 μm.

14. The method of claim 1, wherein the potentiated clinoptilolite is orally administered to said human or animal in the form of a suspension, a powder, a tablet, or a capsule.

15. The method of claim 1, wherein said potentiated clinoptilolite is administered to said human or animal at a dosage rate ranging from about 100 mg to about 6 g per dose.

16. The method of claim 15, wherein said potentiated clinoptilolite is administered to said human or animal at a dosage rate of about 1.5 g per dose.

17. The method of claim 16, further comprising administering said potentiated clinoptilolite to said human or animal multiple times over a single day.

18. The method of claim 1, wherein said potentiated clinoptilolite is administered to said human or animal one to three times over a single day.

19. The method of claim 1, further comprising adsorbing at least one or said metals and said nitrates from a lining of at least one of an alimentary canal and digestive tract of said human or animal.

20. The method of claim 2, wherein said clinoptilolite comprises apertures, and said washing and drying increases the size of said apertures.

21. The method of claim 1, wherein the clinoptilolite that is subject to the washing and drying is raw clinoptilolite comprising 80% to 85% by mass of clinoptilolite, the raw clinoptiloliute further comprising opaline cristobalite and K-feldspar.

* * * * *